United States Patent [19]

Mori

[11] Patent Number: 4,842,356

[45] Date of Patent: Jun. 27, 1989

[54] LIGHT RAY RADIATION DEVICE FOR USE IN MEDICAL TREATMENT OF THE NOSE AND THROAT PASSAGES

[76] Inventor: Kei Mori, 3-16-3-501, Kaminoge, Setagaya-ku, Tokyo, Japan

[21] Appl. No.: 139,493

[22] Filed: Dec. 30, 1987

[30] Foreign Application Priority Data

Apr. 15, 1987 [JP] Japan .................................. 62-94156

[51] Int. Cl.$^4$ .............................................. G02B 6/00
[52] U.S. Cl. .............................. 350/96.10; 128/303.1; 128/397
[58] Field of Search .................. 350/96.10; 128/303.1, 128/397

[56] References Cited

U.S. PATENT DOCUMENTS

| | | |
|---|---|---|
| 4,660,925 | 4/1987 | McCaughan, Jr. ............. 128/397 X |
| 4,693,556 | 9/1987 | McCaughan, Jr. ............. 128/397 X |
| 4,740,047 | 4/1988 | Abe et al. .................... 350/96.10 X |
| 4,744,624 | 5/1988 | Burston ........................ 350/96.10 X |

*Primary Examiner*—John D. Lee
*Assistant Examiner*—Phan T. Heartney
*Attorney, Agent, or Firm*—Jordan and Hamburg

[57] ABSTRACT

A light ray radiation device for use in medical treatment of the nose and throat passages. The device comprises an optical conductor cable or transmitting therethrough light rays corresponding to the visible light ray components of the sun's rays, an elongated light radiator removably connected with the light-emitting end of the optical conductor cable for radiating the light rays transmitted through the optical conductor cable uniformly in the radial direction of the light radiator, and a light radiator holding member through which the light radiator is inserted and which has a ventilating hole.

7 Claims, 3 Drawing Sheets

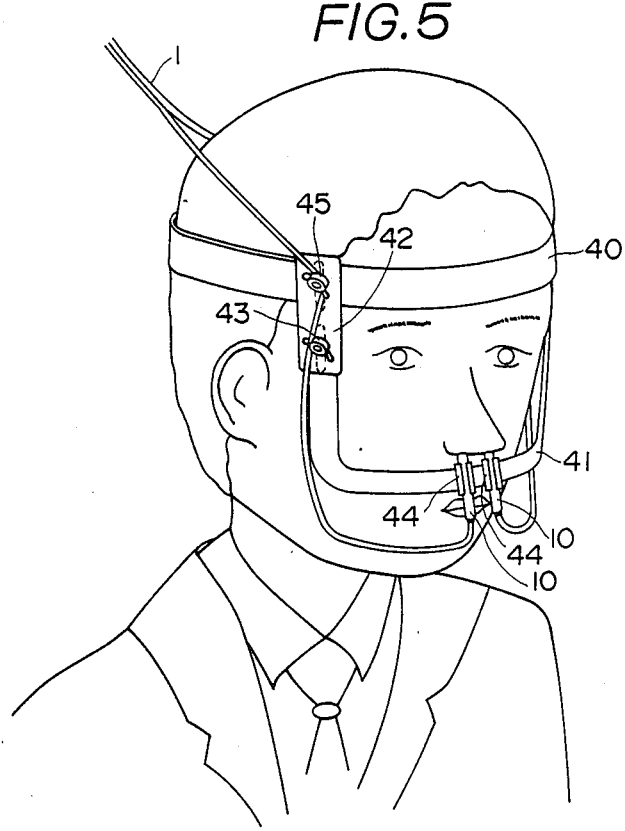
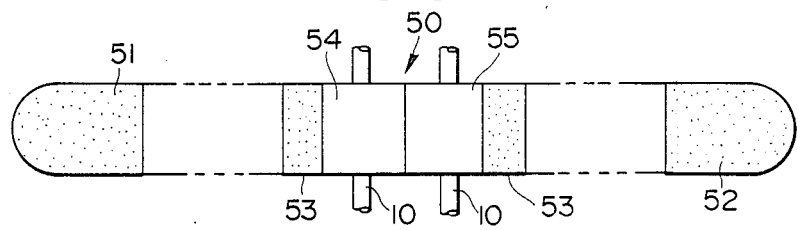
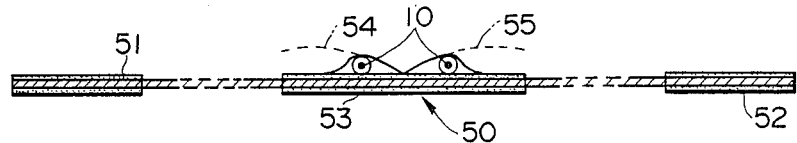

LIGHT RAY RADIATION DEVICE FOR USE IN MEDICAL TREATMENT OF THE NOSE AND THROAT PASSAGES

BACKGROUND OF THE INVENTION

The present invention relates to a light ray radiation device for use in medical treatment of the nose and throat passages, in particular, a visible light ray radiation device for use in medical treatment capable of radiating the light ray components, corresponding to the visible light rays contained in the sun's rays, into the nostrils or throat areas of a human body.

The present applicant has previously proposed various ways to focus the sun's rays or artificial light rays by the use of lenses or the like and to guide the same into an optical conductor cable and thereby to transmit and emit the same onto an optional desired place through an optical conductor. The sun's rays or the artificial light rays transmitted and emitted in such a way are employed for illumination or for other purposes, as for example cultivating plants, chlorella and the like. In the process of doing the above, the visible light rays containing therein neither ultraviolet rays nor infrared rays promote the health of a person by creating a living body reaction or the same prevent the human skin from growing old. Furthermore, there are noticeable beneficial effects of recovering from arthritis, neuralgia, bedsores, rheumatism, burns, skin diseases, injuries, bone fractures, or the like, and for alleviating pain from those same diseases. Such benefical effects have been witnessed by the present applicant.

On the basis of the above-mentioned discovery, the present applicant has previously proposed light ray radiation devices for use in medical treatment and which are capable of giving beauty treatments and which promote the general health of a human being by radiating light rays that correspond to the visible light ray components of the sun's rays and contain which therein no harmful components such as ultraviolet rays, infrared rays, or the like.

A light ray radiation device for use in medical treatment previously proposed by the present applicant comprises an optical conductor cable, a semi-transparent or transparent cylindrical member and a cover member. The solar rays or the artifical light rays are guided into the optical conductor cable at the end portion thereof, and the guided light rays are transmitted therethrough. The light rays corresponding to the visible light ray components of the sun's rays (white light rays) are transmitted into the optical conductor cable in the manner previously proposed by the present applicant. The semi-transparent or transparent cylindrical member is furnished at the light-emitting end portion of the afore-mentioned optical conductor cable and the cover member is provided for closing off one end of the cylindrical member. The light-emitting end portion of the optical conductor cable is attached to the cover member at the almost central portion thereof. The solar ray energy transmitted through the optical conductor cable is discharged into the cylindrical member. At the time of administering medical treatment, the other end of the cylindrical member is put on the part of the body to be cured, or the same is placed opposite to the part to be cured and at the desired interval therefrom. The light rays consisting of the visible light ray components transmitted through the optical conductor cable are radiated onto a diseased part of the body or desired portion to be cured. The light rays to be radiated onto the diseased part of a patient are the light rays corresponding to the visible light ray components of the sun's rays which contain therein neither ultraviolet nor infrared rays. Consequently, it is possible to administer medical treatment without endangering the health of a patient.

SUMMARY OF THE INVENTION

The primary object of the present invention is to provide a radiation device for use in medical treatment capable of insertion into a specific diseased part of a human body and for radiating light rays corresponding to the visible light ray components of the sun into those areas.

It is another object of the present invention to provide a radiation device for use in medical treatment of the nostrils, the throat and/or the like.

The above-mentioned features and other advantages of the present invention will be apparent from the following detailed description which goes with the accompanying drawings.

BRIEF DESCRIPTION OF THE DRAWINGS

FIG. 5 is a perspective view showing a patient equipped with the light radiator; and FIG. 6 and FIG. 7 are views for explaining another embodiment of a light radiator fixing tool.

DESCRIPTION OF THE PREFERRED EMBODIMENTS

Figure 1:
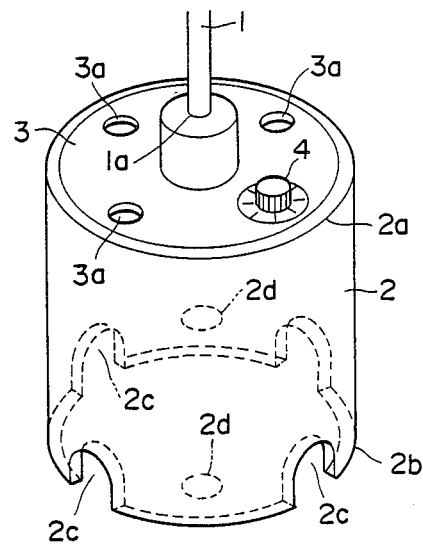
FIG. 1 is a view for explaining an embodiment of the light ray radiation device for use in medical treatment as previously proposed by the present applicant.

FIG. 1 is a construction view for explaining an embodiment of a light ray radiation device or use in medical treatment previously proposed by the present applicant. In FIG. 1, 1 is an optical conductor cable. The sun's rays or the artificial light rays are guided into the optical conductor cable 1 at the end portion thereof not shown in FIG. 1, and the guided light rays are transmitted therethrough. The light rays corresponding to the visible light rays components of the sun's rays are transmitted into the optical conductor cable 1 in the manner previously proposed by the present applicant in various ways. In FIG. 1, 2 is a semi-transparent cylindrical member furnished at the light-emitting end 1a of the afore-mentioned optical conductor cable 1, and 3 is a cover member for closing one end 2a of the cylindrical member 2. The light-emitting end 1a of the optical conductor cable 1 is attached to the cover member 3 at approximately the central portion thereof. The sun's energy transmitted through the optical conductor cable 1 is discharged into the cylindrical member 2. At the time of administering medical treatment, the other end 2b of the cylindrical member is put on the part of a patient to be treated, or the same is placed so as to be opposite to the same part at the desired distance therefrom. The light rays, consisting of the visible light ray components transmitted through the optical conductor cable 1 in such a manner as mentioned before, are radiated onto a diseased part, a desired portion, or other portions needing treatment. The light rays to be radiated onto a diseased part of a patient in such a way are the light rays corresponding to the visible light ray components of the sun's rays. Consequently, it is possible to administer medical treatment without exposing a patient to the harmful effects of ultraviolet or infrared rays.

Figure 2:
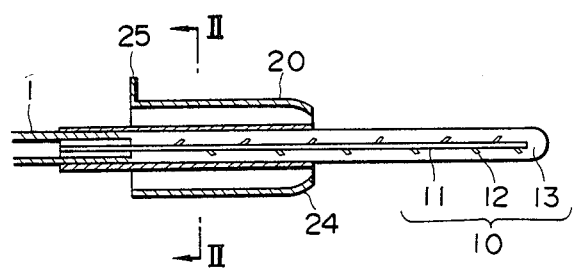
FIG. 2 is a cross-sectional view for explaining an embodiment of a light ray radiation device for use in medical treatment.
Figure 3:
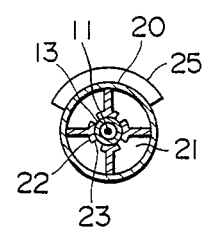
FIG. 3 is a cross-sectional view taken along the line II—II of FIG. 2.

FIG. 2 is a side cross-sectional view for explaining an embodiment of a light ray radiation device for use in medical treatment according to the present invention, and FIG. 3 is a cross-sectional view taken along the line II—II of FIG. 2. In FIG. 2, 1 is an optical conductor cable, 10 a light radiator, and 20 a light radiator holding member. The light rays have the wave-length of the visible light ray components of the sun's rays which contain therein neither ultraviolet rays nor infrared rays. The light radiator 10 is removably connected with the light-emitting end of the optical conductor cable 1. The light rays transmitted through the optical conductor cable 1 are guided into the light radiator 10. In the light radiator 10, the guided light rays are almost uniformly radiated.

The light radiator 10 comprises an optical conductor 11, an adhesive such as epoxy resin 12 uniformly bonded to the outer circumferential portion of the optical conductor 11 having a refractive index equal to or larger than that of the optical conductor 11, and a transparent cover member 13 for covering the optical conductor together with the adhesive 12 bonded thereto, and the same is connected with the light-emitting end of the optical conductor cable 1 when it is employed.

Consequently, the light rays transmitted through the optical conductor cable 1 are guided into the optical conductor 11 of the light radiator 10 and propagate inside the optical conductor 11 toward the tip end portion thereof. During the time of propagation, the light rays are refracted at the adhesive layer portion 12 and discharged from the optical conductor 11. The light rays radiated in such a way are employed for performing medical treatment.

Needless to mention, light radiators 10 of various sizes and shapes are provided in accordance with the form of the patient's body. A suitable one well fitted to the patient is selected among those light radiators and employed for performing medical treatment. Furthermore, if the light radiator 10 is made longer than the ordinary one, it may be also possible to administer medical treatment to the throat portion of a patient. The light radiator 10 is inserted through the light radiator holding member 20 and pressed into contact therewith.

The supporting member 20 is inserted into the nostrils and fixes the light radiator 10 therewith stably. Furthermore, the supporting member 20 has a ventilating hole 21 enabling the patient to breathe through the nose during the medical treatment. And further, notches 23 are formed at a contacting portion 22 of the supporting member 20 which contact with the light radiator 10 causing the contacting portion to have a spring effect. Furthermore, a curved portion 24 is formed at the side for inserting into the nostrils and for the purpose of alleviating pain to the patient when the light radiator 10 is inserted into the nostrils. Moreover, a projection 25 is provided on the holding member 20 and at the side of the connecting portions thereof between the light radiator 10 and the optical conductor cable 1, so that the holding member 20 is prevented from entering the nostrils.

Figure 4:
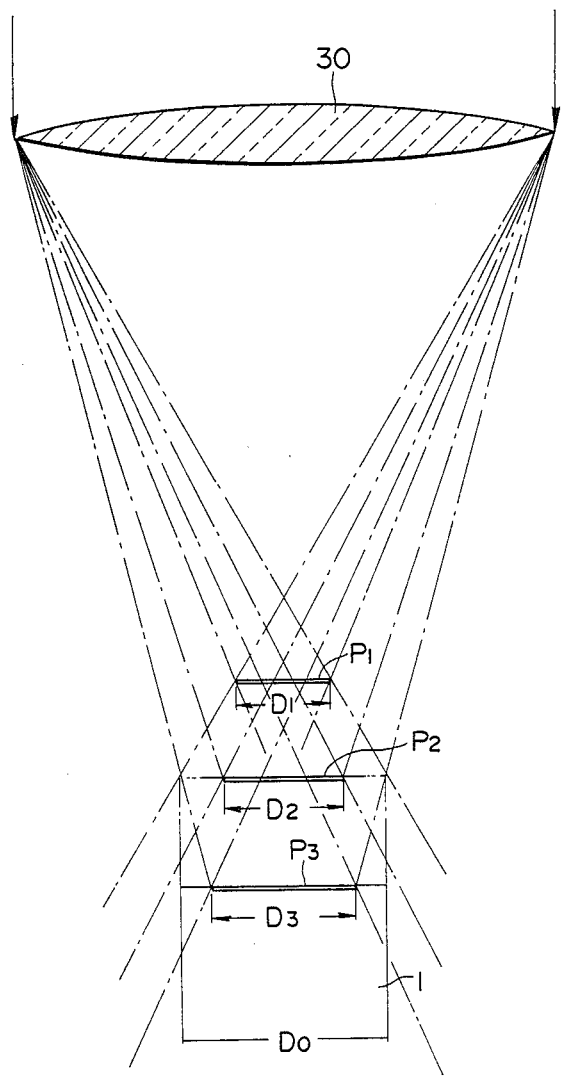
FIG. 4 is an optical view for explaining an embodiment of a visible light ray collecting method preferably applied to the purpose of the present invention.

FIG. 4 is a detailed view for explaining an embodiment of the device which guides the afore-mentioned light rays, corresponding to the visible light ray components of the sun's rays, into the optical conductor cable 1. In FIG. 4, 30 is a lens system consisting of a Fresnel lens or the like, and 1 is an optical conductor cable as mentioned before for guiding thereinto the sun's rays focused by the lens system 30 and for transmitting the guided sun's rays therethrough. In the case of focusing the sun's rays by use of a lens system, the solar image has a central portion consisting of almost white-colored light rays and a circumferential portion containing therein a large amount of light ray components consisting of the wave lengths corresponding to the focal position of the lens system.

Namely, in the case of focusing the sun's rays, the position of the lens system and the size of the solar image will vary in accordance with the wave length of the light rays. For instance, the light rays of the color blue, having a short wave length, make a solar image of diameter $D_1$ at position $P_1$. Furthermore, the light rays of the color green make a solar image of diameter $D_2$ at position $P_2$, and the light rays of the color red make a solar image of diameter $D_3$ at position $P_3$.

Consequently, as shown in FIG. 4, when the light-receiving end-surface of the optical conductor cable 1 is put at position $P_1$, it is possible to collect the sun's rays containing plenty of light rays of the blue color component at the circumferential portion thereof. When the same is put at position $P_2$, it is possible to collect the sun's rays containing plenty of light rays of the green color component at the circumferential portion thereof. When the same is put at position $P_3$, it is possible to collect the sun's rays containing plenty of light rays of the red color component at the circumferential portion thereof. In each case, the diameter of the optical conductor cable is determined by the light ray components to be collected. For instance, the diameters thereof are $D_1$, $D_2$ and $D_3$, respectively, depending on the colors of the light rays to be stressed; i.e. the blue, green and red colors. In such a way, the consumed amount of the optical conductor cable can be reduced, and thereby the sun's rays containing therein plenty of light ray components of the desired color can be collected most effectively. And further, as shown in FIG. 4, if the diameter of the light-receiving end-surface of the optical conductor cable 1 is enlarged to $D_0$, it may be possible to collect visible light rays containing therein all of the wave length components.

The visible light rays transmitted through the optical conductor cable 1 in such a way as mentioned above are guided into the light radiator 10 and discharged almost uniformly in a radial direction by the use of a light radiator 10. Consequently, when the light radiator 10 is inserted into the nostrils or the throat the visible light rays are radiated onto the mucous membrane or the skin's surface of the nasal passages or the throat. Thereby, the diseased part of a patient can be reached and cured.

FIG. 5 is a perspective view showing how a patient is equipped with the light radiator as indicated above. The light rays transmitted through the optical conductor cable 1, as mentioned before, are guided into the light radiator 10 and discharged onto the surfaces of the nasal passages or the throat area from the light radiator 10. When the patient receives medical treatment while lying down, the light-radiator 10 can be fixed to a desired position by the use of the afore-mentioned holding means 20. However, when the patient receives medical treatment while standing or sitting down on a chair, the light radiator 10 tends to slip down. Therefore, it is necessary to prevent it from slipping down.

The example shown in FIG. 5 illustrates the case in which the patient is equipped with the light ray radiation device for use in medical treatment while standing or sitting down on a chair. In FIG. 5, 40 is a forehead band, 41 a U-shaped suspension band, 42 a support member for suspending the suspension band 41 from the forehead band 40 and for fixing the same thereto, wherein the length of the suspension band 41 can be adjusted in an up-and-down direction by the use of a fixing screw 43, 44 is a fixing spring for fixing the light radiator 10, and 45 a fixing screw for fixing the optical conductor cable 1. The position of the U-shaped suspension band 41 is adjusted in the up-and-down direction by the use of the fixing screw 43 in such a way that the bottom portion of the U-shaped suspension band 41 is located at a place near the nostrils. The fixing spring 44 clippingly holds the light radiator 10 and fixes it onto a pre-determined position. On that occasion, the fixing screw 45 fixes the optical conductor cable 1 onto the support member 42 in order to prevent the light radiator 10 from being pulled by an unexpected force applied thereto from the outside.

Furthermore, the fixing tool of the light radiator isn't limited only to the one shown in FIG. 5. For instance, as shown in FIGS. 6, 7 (FIG. 6 is a plan view and FIG. 7 is a side view, respectively of a light radiator fixing tool.), surface fasteners 51 and 52 are provided at both end portions of a cloth band 50, and an other surface fastener 53 is also provided at the one-direction surface on the central portion of the cloth band 50. Furthermore, a pair of surface fasteners 54 and 55 are provided symmetrically on the central portion thereof so as to be opposite to the surface fastener 53. The light radiator consists of a pair of radiators. It may be possible that one of them be fixed onto the cloth band 50 by the use of the fasteners 53 and 54, and that another be fixed thereon by the use of fasteners 53 and 55. Otherwise, various other fixing tools can be set depending on the desired purpose.

As is apparent from the foregoing description, according to the present invention, the mucous membrane or the skin's surface in the nostrils or the throat area is activated by radiating thereon the light rays containing no harmful rays, and thereby a beneficial effect can be obtained from the medical treatment. In particular, since the light radiator is inserted into the nostrils and fixed onto the surface thereof through a holding member having a ventilating hole, the patient can breathe easily. And further, the patient can receive medical treatment without feeling any pain.

I claim:

1. A light rays radiation device for use in medical treatment of a person's body passage such as the nose and throat, comprising an optical conductor cable for transmitting the visible light rays component of solar rays from which harmful ultraviolet and infrared rays have been excluded, a light radiator means removably connected to said cable, said light radiator means comprising a transparent cover member and an elongated optical conductor disposed within said transparent cover member such that said visible light rays are transmitted through said cable to said optical conductor, said optical conductor having discharge means spaced along its longitudinal length for discharging said transmitted light rays such that said transmitted light rays are thereby radiated outwardly along the longitudinal length of said optical conductor, said cover member having an outer longitudinal end section and an inner longitudinal end section, and a holder means for supporting said inner longitudinal end section of said cover member within said passage, said holder means comprising a generally cylindrical holder tube through which said inner longitudinal end section of said cover member extends, said holder tube being spaced from said inner longitudinal end section of said cover member to define an annular space therebetween, said holder means further comprising spaced support parts disposed in said annular space and extending between said holder tube and said inner longitudinal end section of said cover member, said holder tube having longitudinal ends which are open and which together with said annular space define ventilating passages which extend longitudinally through said annular space and which are disposed between said support parts, whereby said holder tube is insertable into said passage such that said outer longitudinal end section extends further into said passage than said holder tube as said holder tube supports said radiating means in said passage and said light rays from said light radiating means are radiated into said passage.

2. A light rays radiation device according to claim 1, wherein said holder tube is made of a transparent material.

3. A light rays radiation device according to claim 1, whereby said holder tube is made of an elastic material.

4. A light rays radiation device according to claim 1, wherein said holder tube has an inner longitudinal end and an outer longitudinal end, and a projection extending radially outwardly from said outer longitudinal end.

5. A light rays radiation device according to claim 4, wherein said outer longitudinal end of said holder tube has an outer circumference having a first circumferential portion and a second circumferential portion, said projection extending radially outwardly from said first circumferential portion, said holder tube having an outer cylindrical surface, said second circumferential portion being flush with said outer cylindrical surface.

6. A light rays radiation device according to claim 4, wherein said holder tube has an inner longitudinal end portion juxtaposed to said inner longitudinal end, said inner longitudinal end portion curving radially inwardly as said inner longitudinal end is approached.

7. A light rays radiation device according to claim 1, wherein said support parts each comprise a radial extending portion having an inner radial end and a partial cylindrical portion on said inner radial end, said partial cylindrical portion being in contact with said cover member.

* * * * *